(12) United States Patent
Scarborough (10) Patent No.: US 6,616,698 B2
(45) Date of Patent: Sep. 9, 2003

(54) BONE GRAFT AND GUIDED BONE REGENERATION METHOD

(75) Inventor: Nelson L. Scarborough, Ocean, NJ (US)

(73) Assignee: Osteotech, Inc., Eatontown, NJ (US)

(*) Notice: Subject to any disclaimer, the term of this patent is extended or adjusted under 35 U.S.C. 154(b) by 0 days.

(21) Appl. No.: 09/810,107

(22) Filed: Mar. 16, 2001

(65) Prior Publication Data

US 2001/0014831 A1 Aug. 16, 2001

Related U.S. Application Data

(63) Continuation-in-part of application No. 09/211,310, filed on Dec. 14, 1998, now abandoned.

(51) Int. Cl.[7] .................................................. A61F 2/28
(52) U.S. Cl. .............................. 623/23.51; 623/23.61; 623/23.63
(58) Field of Search ..................... 623/23.51, 20.17, 623/20.16, 23.63, 23.61

(56) References Cited

U.S. PATENT DOCUMENTS

| | | |
|---|---|---|
| 2,516,438 A | 7/1950 | Wheeler |
| 4,172,128 A | 10/1979 | Thiele et al. |
| 4,209,434 A | 6/1980 | Wilson et al. |
| 4,291,013 A | 9/1981 | Wahlig et al. |
| 4,294,753 A | 10/1981 | Urist |
| 4,430,760 A | 2/1984 | Smestad |
| 4,440,750 A | 4/1984 | Glowacki et al. |
| 4,563,489 A | 1/1986 | Urist |
| 4,595,713 A | 6/1986 | St. John |
| 4,620,327 A | 11/1986 | Caplan et al. |
| 4,678,470 A | 7/1987 | Nashef et al. |
| 4,795,467 A | 1/1989 | Piez et al. |
| 4,863,472 A | 9/1989 | Törmäla et al. |
| 4,919,939 A | 4/1990 | Baker |
| 4,950,296 A | 8/1990 | McIntyre |
| 4,961,707 A | 10/1990 | Magnusson et al. |
| 5,073,373 A | 12/1991 | O'Leary et al. |
| 5,197,882 A | 3/1993 | Jernberg |
| 5,207,710 A | 5/1993 | Chu et al. |
| 5,314,476 A * | 5/1994 | Prewett et al. ........... 623/23.63 |
| 5,314,478 A | 5/1994 | Oka et al. |
| 5,366,507 A * | 11/1994 | Sottosanti ................. 424/424 |
| 5,368,859 A | 11/1994 | Dunn et al. |
| 5,425,639 A | 6/1995 | Anders |
| 5,447,725 A | 9/1995 | Damani et al. |
| 5,455,041 A | 10/1995 | Genco et al. |
| 5,480,436 A | 1/1996 | Bakker et al. |
| 5,507,813 A * | 4/1996 | Dowd et al. ............. 623/23.63 |
| 5,510,396 A | 4/1996 | Prewett et al. |

(List continued on next page.)

FOREIGN PATENT DOCUMENTS

| | | |
|---|---|---|
| DE | 4434459 | 4/1996 |
| EP | 0693523 | 1/1996 |
| FR | 2691901 | 12/1993 |

OTHER PUBLICATIONS

Marlin E. Gher et al., Bone Grafting and Guided Bone Regeneration for Immediate Dental Implants in Humans, J. Periodontol 1994; 65:881–891.

(List continued on next page.)

Primary Examiner—Paul B. Prebilic
Assistant Examiner—Crystal Gilpin
(74) Attorney, Agent, or Firm—Dilworth & Barrese, LLP (57) ABSTRACT

An implantable, biocompatible, osteogenic bone graft comprises at least one zone of impermeability to soft tissue ingrowth which is integral with the bone graft. Application of the bone graft to a bone repair site leads to selective rapid new bone ingrowth and inhibits or prevents soft tissue, e.g., gingival, epithelial, connective and/or muscle tissue, ingrowth in those areas adjacent to the zone(s) of impermeability to soft tissue ingrowth. The bone graft can be employed in a wide variety of bone repair procedures.

35 Claims, 6 Drawing Sheets

U.S. PATENT DOCUMENTS

| | | | |
|---|---|---|---|
| 5,567,806 A | 10/1996 | Abdul-Malak et al. | |
| 5,656,593 A | 8/1997 | Kuberasampath et al. | |
| 5,700,479 A | 12/1997 | Lundgren | |
| 5,707,962 A | 1/1998 | Chen et al. | |
| 5,727,945 A | 3/1998 | Dannenbaum | |

OTHER PUBLICATIONS

Product Literature for Gore Resolut XT, bioabsorbable membrane from Gore Regenerative Technologies, Palm Beach Gardens, FL (1998).

Product Literature for Bio–Gide®, resorbable barrier membrane from Osteo Health Co., Division of Luitpold Pharmaceutical, Inc. (1998).

James T. Mellonig, DDS, MS, Bone Allografts in Periodontal Therapy, Clinical Orthopaedics and Related Research, No. 324, Mar., 1996.

Thitiwan Teparat et al., Clinical Comparison of Bioabsorbable Barriers With Non–Resorbable Barriers in Guided Tissue Regeneration in the Treatment of Human Intrabony Defects, J Periodontal, Jun. 1998.

Michael S. Block, DMD, et al., Bone Maintenance 5 to 10 years After Sinus Grafting, J Oral Maxillofac Surg, vol. 56, pp. 706–714, 1998.

S. Parma–Benfenati et al., Histologic Evaluation of New Attachment Utilizing a Titanium–Reinforced Barrier Membrane in a Mucogingival Recession Defect. A Case Report, J Periodontal, Jul. 1998.

Bobyn et al., The Optimum Pore Size for the Fixation of Porous–Surfaced Metal Implants by Ingrowth of Bone, Clinical Orthopaedics and Related Research, pp. 263–270 (1980.

\* cited by examiner

BONE GRAFT AND GUIDED BONE REGENERATION METHOD

CROSS REFERENCE TO RELATED APPLICATIONS

This application is a continuation-in-part of U.S. patent application Ser. No. 09/211,310 filed Dec. 14, 1998 now abandoned, from which priority is claimed.

FIELD OF THE INVENTION

This invention relates to a bone graft, to a method of making the bone graft and to a guided bone regeneration (GBR) method employing the bone graft. More particularly, this invention relates to an implantable, biocompatible osteogenic bone graft possessing at least one zone of impermeability to soft tissue ingrowth, to a method of making such bone graft and to a guided bone regeneration method that promotes bone cell ingrowth preferentially over soft tissue ingrowth.

BACKGROUND OF THE INVENTION

Conventionally, bone tissue regeneration is achieved by filling a bone repair site with a bone graft. Over time, the bone graft is incorporated by the host and new bone remodels the bone graft. The bone grafts currently in use, however, do not always provide reliable bone tissue regeneration because they are not capable of inducing sufficient bone growth before competitive, faster-growing soft tissue and epithelial cells fill the bone repair site. To overcome this problem, current standard procedures employ a barrier material which is applied over the bone graft to exclude competitive cells. This procedure is known as guided bone regeneration (GBR) or guided tissue regeneration (GTR) and is documented to be useful as an adjunct to the bone graft procedure.

By way of example, a common problem in periodontal surgery is maintenance of bone tissue around teeth or in those areas where teeth have been removed and dental implants will subsequently be placed. Demineralized bone matrix (DBM) is a common material used to promote bone formation in these areas. DBM works well due to its osteoinductive and osteoconductive healing properties. A common practice is to extract a tooth and then place DBM back into the socket such that new bone will then grow into the socket allowing a solid foundation for subsequent metallic implant placement. A common adjunct to this procedure is the placement of a barrier membrane over the surface of the bone graft such that ingrowth of soft tissue from the gingiva and other surrounding areas can be prevented.

Several problems are associated with barrier membranes. Their surgical placement is tedious, they have a tendency to become infected and they are relatively costly. After the initial surgical procedure, removal of the membrane to prevent effects such as inflammation and infection is required. A well known commercially available membrane is made of expanded polytetrafluoroethylene (e-PTFE) film by WL Gore, Inc. Recently, bioabsorbable membranes fabricated from collagen or other polymers such as polyglycolates have become available. While these membranes obviate the need for a subsequent removal operation, they are difficult to handle and implant and do not always remain intact long enough to initiate sufficient bone growth.

SUMMARY OF THE INVENTION

It is an object of the present invention to provide a bone graft which promotes bone cell ingrowth preferentially over soft tissue ingrowth in a bone repair procedure.

It is a further object of the present invention to provide a bone graft which promotes bone cell ingrowth below the bone line and prevents soft tissue ingrowth above the bone line in a bone repair procedure.

It is yet a further object of the present invention to provide a GBR method which obviates the need for a barrier membrane in a bone repair procedure.

It is yet an even further object of the present invention to provide a bone graft which occludes soft tissue ingrowth while promoting bone formation within the bone repair site.

It is still a further object of the present invention to provide a bone graft possessing rigidity in order to maintain space for the bone formation zone. Rigidity prevents displacement due to loads placed on the bone repair site.

In keeping with these and related objects of this invention, an implantable, biocompatible osteogenic bone graft is provided which comprises at least one zone of impermeability to soft tissue ingrowth wherein said zone is integral with the bone graft. The bone graft of this invention can be formed by providing a coherent mass of bone particles and occluding a portion of a surface of the coherent mass of bone particles to provide a zone of impermeability to soft tissue ingrowth on such surface.

Application of the foregoing bone graft to a bone repair site leads to selective rapid new bone ingrowth and inhibits or prevents soft tissue, e.g., gingival, epithelial, connective and/or muscle tissue, ingrowth in those areas adjacent to the zone(s) of impermeability to soft tissue ingrowth.

The term "coherent" as applied to the mass of bone particles refers to the ability of the bone particles to adhere to each other either mechanically, e.g., by entanglement, or by use of a biocompatible matrix whether the mass of bone particles is in the dry or wetted, e.g., hydrated, state.

The term "osteogenic" as applied to the bone graft of this invention shall be understood as referring to the ability of the bone graft to enhance or accelerate the ingrowth of new bone tissue by one or more mechanisms such as osteogenesis, osteoconduction and/or osteoinduction.

The term "occluding" as utilized herein shall be understood to refer to any operation or process which reduces the porosity of a surface area of the bone graft to render such surface area substantially impermeable to the ingrowth of soft tissue.

The terms "impermeable" and "occlusive" are utilized herein interchangeably and shall be understood as referring to any zone, i.e., surface region, of the bone graft of this invention which possesses an average pore size which substantially prevents the ingrowth of soft tissue. Average pore sizes of from about 3 microns or less are known to prevent ingrowth of soft tissue. The zone of impermeability can include pores larger than 3 microns as long as the presence of such pores does not permit soft tissue ingrowth. Generally, average pore sizes above 30 microns are believed to permit soft tissue ingrowth.

The term "integral" as utilized herein is intended to differentiate the bone graft of this invention from bone grafts which are combined with a separate barrier membrane material. In the instant invention, the bone graft and the zone of impermeability are integral with one another, i.e., they are formed from the same material and are indivisibly interconnected so as to form a single, unified whole.

The term "rigidity" as utilized herein refers to the property of the bone graft of resisting displacement or deformation when load is applied thereto. This ability to hold the appropriate space is important to preserve adequate bone volume after healing occurs.

BRIEF DESCRIPTION OF THE DRAWINGS

Various embodiments are described below with reference to the drawings wherein:

FIG. 3b shows an enlarged view of the bone graft of FIG. 3a;

FIG. 4b is an isometric view depicting the bone graft being implanted into the periodontal extraction socket of FIG. 4a;

FIG. 4c shows an enlarged view of the bone graft of FIG. 4a;

DESCRIPTION OF THE PREFERRED EMBODIMENTS

To fabricate the bone graft of this invention, a coherent mass of bone particles is first produced. Thereafter, a portion of the surface area of the coherent mass is occluded to reduce the porosity of the surface area so as to render that surface area impermeable to the ingrowth of soft tissue.

Production of the Coherent Mass of Bone Particles

The bone particles employed in the production of the coherent mass can be powdered bone particles possessing a wide range of particle sizes ranging from relatively fine powders to coarse grains and even larger chips. Thus, e.g., the bone particles can range in average particle size from about 0.05 to about 1.2 cm and preferably from about 0.1 to about 1 cm and possess an average median length to median thickness ratio of from about 1:1 to about 3:1. If desired, the bone particles can be graded into different sizes to reduce or eliminate any less desirable size(s) of particles which may be present.

Alternatively, or in combination with the aforementioned bone powder, bone particles generally characterized as "elongate" and possessing relatively high median length to median thickness ratios can be utilized herein. Such elongate particles can be readily obtained by any one of several methods, e.g., by milling or shaving the surface of an entire bone or relatively large section of bone. Employing a milling technique, one can obtain a mass of elongate bone particles containing at least about 60 weight percent, preferably at least about 70 weight percent and most preferably at least about 80 weight percent of bone particles possessing a median length of from about 2 to about 200 mm or more and preferably from about 10 to about 100 mm, a median thickness of from about 0.05 to about 2 mm and preferably from about 0.2 to about 1 mm and a median width of from about 1 mm to about 20 mm and preferably from about 2 to about 5 mm. These bone particles can possess a median length to median thickness ratio of at least about 50:1 up to about 500:1 or more and preferably from about 50:1 to about 100:1 and a median length to median width ratio of from about 10:1 and about 200:1 and preferably from about 50:1 to about 100:1. Another procedure for obtaining the elongate bone particles herein, particularly useful for pieces of bone of up to about 100 mm in length, is the bone processing mill described in commonly assigned U.S. Pat. No. 5,607,269. Use of this bone mill results in the production of long, thin strips which quickly curl lengthwise to provide tubular-like bone particles. If desired, the mass of bone particles can be graded into different sizes to reduce or eliminate any less desirable size(s) of particles which may be present. In overall appearance, the elongate bone particles can be described as filaments, fibers, threads, slender or narrow strips, etc.

The bone particles employed in the practice of the present invention can be obtained from cortical, cancellous and/or corticocancellous bone which may be of autogenous, allogenic and/or xenogeneic origin. Porcine and bovine bone are particularly advantageous types of xenogeneic bone tissue which can be used individually or in combination as sources for the bone particles.

The powdered and/or elongate bone particles are optionally subjected to demineralization in accordance with known and conventional procedures in order to reduce their inorganic mineral content. Demineralization methods remove the inorganic mineral component of bone by employing acid solutions. Such methods are well known in the art, see for example, Reddi et al., *Proc. Nat. Acad. Sci.* 69, pp1601–1605 (1972), incorporated herein by reference. The strength of the acid solution, the shape of the bone particles and the duration of the demineralization treatment will determine the extent of demineralization. Reference in this regard may be made to Lewandrowski et al., *J. Biomed Materials Res,* 31, pp365–372 (1996), also incorporated herein by reference.

As utilized herein, the phrase "superficially demineralized" refers to bone particles possessing at least about 90 weight percent of their original inorganic mineral content. The phrase "partially demineralized" refers to bone particles possessing from about 8 to about 90 weight percent of their original inorganic mineral content and the phrase "fully demineralized" refers to bone particles possessing less than about 8, preferably less than about 1, weight percent of their original inorganic mineral content. The term "demineralized" used alone is intended to cover any one of the foregoing types of demineralized bone particles. Mixtures of one or more of the foregoing types of demineralized bone particles can be employed. Moreover, one or more of the foregoing types of demineralized bone particles can be employed in combination with non-demineralized bone particles, i.e., bone particles that have not been subjected to a demineralization process. It will be understood by those skilled in the art that fully demineralized bone particles yield a more porous mass compared to non-demineralized or superficially demineralized bone particles.

When prepared in whole or in part from bone particles that are only superficially demineralized or nondemineralized, the bone graft herein will tend to possess a fairly high compression strength, e.g., one approaching that of natural bone. Accordingly, when a bone graft exhibiting rigidity, e.g., a compression strength of on the order of from about 5 to about 200 MPa, preferably from about 20 to about 100 MPa, more preferably from about 25 to about 75 MPa, is desired, superficially demineralized bone particles and/or nondemineralized bone particles can be advantageously employed.

In a preferred demineralization procedure, the bone particles are subjected to a defatting/disinfecting step which is followed by an acid demineralization step. A preferred defatting/disinfectant solution is an aqueous solution of ethanol, the ethanol being a good solvent for lipids and the water being a good hydrophilic carrier to enable the solution to penetrate more deeply into the bone particles. The aqueous ethanol solution also disinfects the bone by killing vegetative microorganisms and viruses. Ordinarily, at least about 10 to about 40 percent by weight of water (i.e., about 60 to about 90 weight percent of defatting agent such as alcohol) should be present in the defatting disinfecting solution to produce optimal lipid removal and disinfection within the shortest period of time. The preferred concentration range of the defatting solution is from about 60 to about 85 weight percent alcohol and most preferably about 70 weight percent alcohol. Following defatting, the bone particles are immersed in acid over time to effect their demineralization. Acids which can be employed in this step include inorganic acids such as hydrochloric acid and organic acids such as peracetic acid. After acid treatment, the demineralized bone particles are rinsed with sterile water for injection to remove residual amounts of acid and thereby raise the pH. Where elongate bone particles are employed, some entanglement of the wet demineralized bone particles will result. The wet demineralized bone particles can then be immediately shaped into any desired configuration or stored under aseptic conditions, advantageously in a lyophilized state, for processing at a later time.

If desired, the bone particles can be modified in one or more ways, e.g., their protein content can be augmented or modified as described in U.S. Pat. Nos. 4,743,259 and 4,902,296, the contents of which are incorporated by reference herein.

The bone particles can be admixed with one or more substances such as binders, fillers, plasticizers, biostatic/biocidal agents, surface active agents, and the like, prior to, during, or after shaping the particles into a desired configuration. One or more of such substances can be combined with the bone particles by soaking or immersing the bone particles in a solution or dispersion of the desired substance, by physically admixing the bone particles and the desired substance, and the like. Suitable binders include cyanoacrylates, epoxy-based compounds, dental resin sealants, dental resin cements, glass ionomer cements, polymethyl methacrylate, gelatin-resorcinol-formaldehyde glues, collagen-based glues, acrylic resins, cellulosics, bioabsorbable polymers such as polyglycolide, polylactide, glycolide-lactide copolymers, polycaprolactone, polyanhydrides, polycarbonates, polyorthoesters, polyamino acids, polycyanoacrylates, polyhydroxybutyrate, polyhydroxyvalyrate, polyphosphazenes, and polyvinylpyrrolidone, etc. Suitable fillers include bone powder, demineralized bone powder, hydroxyapatite, tricalcium phosphate, Bioglass® and other calcium phosphate materials, etc. Suitable plasticizers include liquid polyhydroxy compounds such as glycerol, monoacetin, diacetin, etc. Suitable biostatic/biocidal agents include antibiotics, povidone, sugars, mucopolysaccharides, etc. Suitable surface active agents include the biocompatible nonionic, cationic, anionic and amphoteric surfactants. It will be understood by those skilled in the art that the foregoing list is not intended to be exhaustive and that other materials may be admixed with bone particles within the practice of the present invention.

Any of a variety of bioactive substances can be incorporated in, or associated with, the bone particles either before, during or after fabrication of the bone graft disclosed herein. Thus, one or more of such substances can be combined with the bone particles by soaking or immersing the bone particles in a solution or dispersion of the desired substance(s). Bioactive substances include physiologically or pharmacologically active substances that act locally or systemically in the host.

Bioactive substances which can be readily combined with the bone particles include, e.g., collagen, insoluble collagen derivatives, etc., and soluble solids and/or liquids dissolved therein, e.g., antiviricides, particularly those effective against HIV and hepatitis; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamicin, etc.; biocidal/biostatic sugars such as dextran, glucose, etc.; amino acids, peptides, vitamins, inorganic elements, co-factors for protein synthesis; hormones; endocrine tissue or tissue fragments, synthesizers; enzymes such as collagenase, peptidases, oxidases, etc., polymer cell scaffolds with parenchymal cells, angiogenic drugs and polymeric carriers containing such drugs; collagen lattices; antigenic agents; cytoskeletal agents; cartilage fragments, living cells such as chondrocytes, bone marrow cells, mesenchymal stem cells, natural extracts, genetically engineered living cells or otherwise modified living cells, DNA delivered by plasmid or viral vectors, tissue transplants, demineralized bone powder, autogenous tissues such as blood, serum, soft tissue, bone marrow, etc.; bioadhesives, bone morphogenic proteins (BMPs); osteoinductive factor (IFO); fibronectin (FN); endothelial cell growth factor (ECGF); cementum attachment extracts (CAE); ketanserin; human growth hormone (HGH); animal growth hormones; epidermal growth factor (EGF); interleukin-1 (IL-1); human alpha thrombin; transforming growth factor (TGF-beta); insulin-like growth factor (IGF-1); platelet derived growth factors (PDGF); fibroblast growth factors (FGF, bFGF, etc.); periodontal ligament chemotactic factor (PDLGF); somatotropin; bone digesters; antitumor agents; immuno-suppressants; permeation enhancers, e.g., fatty acid esters such as laureate, myristate and stearate monoesters of polyethylene glycol, enamine derivatives, alpha-keto aldehydes, etc.; and nucleic acids. The amounts of such optionally added substances can vary widely with optimum levels being readily determined in a specific case by routine experimentation.

To fabricate the coherent mass of bone particles, a quantity of bone particles, of which at least about 60 weight percent preferably constitute demineralized elongate bone particles as described above, is mixed with a suitable biocompatible liquid, e.g., water, organic protic solvent, aqueous solution such as physiological saline, liquid polyhydroxy compounds etc., which can optionally contain one or more substances such as binders, fillers, plasticizers, biostatic/biocidal agents, surface active agents, bioactive substances, etc., as previously described to form a slurry or paste. Where elongate bone particles are employed some entanglement of the wet bone particles will result. Excess liquid is then removed from the slurry or paste, e.g., by applying the slurry or paste to a form such as a flat sheet, mesh screen or three-dimensional mold and draining away excess liquid. Functionally, the biocompatible liquid serves to provide a coherent mass whose consistency can be described as shape-sustaining but readily deformable, e.g., putty. Optionally, the bone particles can be dried at a suitable temperature, e.g., one ranging from about 30° to about 70° C., preferably from about 40° to about 50° C., for 1 to 3 hours, and then lyophilized under conditions that are well known in the art, e.g., a shelf temperature of from about −20° to about −35° C., a vacuum of from about 150 to about 100 mTorr for a period of time ranging from about 4 to about 48 hours. The drying and lyophilization steps will result in the production of a coherent mass of bone particles which is relatively strong when dry and flexible when wetted or hydrated. In an alternative embodiment herein, the coherent mass can be subjected to a compressive force, e.g., of up to about 50,000 psi, during and/or after the step of removing excess liquid and/or while the drained-but-still-wet bone particles are being dried. If desired, the compressed coherent mass can be lyophilized to provide an extremely strong and rigid mass.

Where a mold, e.g., a cylindrical mold, is employed to fabricate the coherent mass of bone particles, the walls of the mold can be coated with a slurry or paste containing partially and/or fully demineralized bone particles followed by addition of a slurry or paste containing non-demineralized and/or superficially demineralized bone particles (or vice versa) to provide a bone graft which contains at least one discrete region, e.g., an outer surface, composed of partially and/or fully demineralized bone particles and at least one discrete region, e.g., a core, composed of non-demineralized and/or superficially demineralized bone particles. In this manner, the differential in compressive strength, porosity, osteogenicity and other properties between partially and/or fully demineralized bone particles on the one hand and non-demineralized and/or superficially demineralized bone particles on the other hand can be exploited. For example, where the bone graft is employed in a load-bearing situation, non-demineralized and/or superficially demineralized bone particles can be concentrated in that region of the bone graft which will be subjected to applied load at the implant site.

The resulting coherent mass of bone particles can assume a determined or regular form or configuration such as a tooth, tooth root, sheet, plate, disk, tunnel, cone, pin, screw, tube, to name but a few. Of course, the coherent mass can be machined or shaped by any suitable mechanical shaping means. Computerized modeling can, for example, be employed to provide an intricately-shaped coherent mass which is custom-fitted to the bone repair site with great precision. In a preferred embodiment, the coherent mass possesses the configuration of a tooth or tooth root.

The coherent mass fabricated in accordance with this disclosure will possess a bone particle content ranging from about 20 to about 100 weight percent, preferably from about 30 to about 90 weight percent and more preferably from about 40 to about 85 weight percent, based on the weight of the entire coherent mass. It will be understood by those skilled in the art that coherent masses possessing a putty-like consistency will possess lower amounts of bone particles, on a weight-by-weight basis, compared to coherent masses which are subjected to the drying and lyophilizing and/or compression steps described above.

Preferred biocompatible liquids for forming the slurry or paste of bone particles include liquid polyhydroxy compounds and their esters alone or in combination with water and/or surfactants, e.g., the Pluronics® series of nonionic surfactants. The preferred polyhydroxy compounds possess up to about 12 carbon atoms and, where their esters are concerned, are preferably the monoesters and diesters. Specific polyhydroxy compounds of the foregoing type include glycerol and its monoesters and diesters derived from low molecular weight carboxylic acids, e.g., monoacetin and diacetin (respectively, glycerol monoacetate and glycerol diacetate), ethylene glycol, diethylene glycol, triethylene glycol, 1,2-propanediol, trimethylolethane, trimethylolpropane, pentaerythritol, sorbitol, and the like. Of these, glycerol is especially preferred as it exhibits a particularly pronounced capability for dissolving osteogenic proteins (e.g., BMP) present in the bone particles and enhancing the availability of these proteins at the bone repair site. Mixtures of polyhydroxy compounds or esters, e.g., sorbitol dissolved in glycerol, glycerol combined with monoacetin and/or diacetin, etc., are also useful.

Where, in a particular composition, the bone particles have a tendency to quickly or prematurely separate from the carrier or to otherwise settle out from the composition such that application of a fairly homogeneous composition is rendered difficult or inconvenient, it can be advantageous to include within the composition a substance whose thixotropic characteristics prevent or reduce this tendency. Thus, e.g., where the biocompatible liquid is glycerol and separation of bone particles occurs to an excessive extent where a particular application is concerned, a thickener such as a solution of polyvinyl alcohol, polyvinylpyrrolidone, cellulosic ester such as hydroxypropyl methylcellulose, carboxy methylcellulose, pectin, food-grade texturizing agent, gelatin, dextran, collagen, starch, hydrolyzed polyacrylonitrile, hydrolyzed polyacrylamide, polyelectrolyte such as polyacrylic acid salt, hydrogels, chitosan, other materials that can suspend particles, etc., can be combined with the biocompatible liquid in an amount sufficient to significantly improve the suspension-keeping characteristics of the composition.

Occluding a Portion of the Surface Area of the Coherent Mass

The resulting coherent mass of bone particles is then subjected to an operation or process which occludes a selected surface area of the coherent mass to provide a skin or barrier which is impermeable to soft tissue ingrowth. This operation can be performed by heating a portion of the surface area of the coherent mass, by cross-linking a portion of the surface area of the coherent mass and/or by applying one or more biocompatible substances to a portion of the surface area of the coherent mass to provide a microporous layer thereon. It will be understood that combinations of one or more of the foregoing operations can be employed, e.g., heating followed by cross-linking, cross-linking followed by heating, cross-linking followed by application of biocompatible substance, etc. It will also be understood that any of these operations can be performed on the coherent mass before or after the optional drying and lyophilizing steps described above. Thus, e.g., the coherent mass can be subjected to the heating operation to occlude a portion of the surface area of the coherent mass followed by lyophilization of the occluded coherent mass.

Where heating is employed to occlude a surface area of the bone graft, temperatures ranging from about 30 to about 80° C. can be advantageously employed. It has been observed that heating the coherent mass of bone particles within this temperature range produces a tough "skin" or barrier on the outer surface of the coherent mass. As demonstrated in Example 2 below, this skin or barrier effectively acts as a barrier to soft tissue ingrowth. Thus, the bone graft of this invention permits slower-growing bone tissue to remodel the bone graft before competitive, faster-growing soft tissue invades the bone repair site. It will be understood that a variety of heating techniques can be advantageously employed to heat a selected surface area of the coherent mass of bone particles. In one embodiment, the shaped coherent mass of bone particles is compressed against a suitable surface, e.g., smooth Tyvek or stainless steel surface, which is heated at elevated temperature, e.g., a temperature within the range of from about 30 to about 80° C., preferably from about 50 to about 70° C., for a suitable period of time, e.g., for about 1 to about 60 minutes, preferably about 3 to about 10 minutes. In another embodiment, a coherent mass of bone particles can be implanted at a bone repair site and heated directly at the bone repair site using any suitable means, e.g., an electro-cautery device, to occlude a portion of the surface area of the coherent mass in situ. In another embodiment, a coherent mass having a putty-like consistency is contoured to a bone repair site and either heated in situ or removed and then heated to provide an occluded surface area which is impermeable to soft tissue ingrowth. Upon removal, the bone graft possessing a putty-like consistency can be post-treated, e.g., compressed and/or lyophilized, to impart rigidity to the bone graft prior to implantation.

Crosslinking can be effected by a variety of known methods including chemical reaction, the application of energy such as radiant energy, which includes irradiation by UV light or microwave energy, drying and/or heating and dye-mediated photo-oxidation; dehydrothermal treatment in which water is slowly removed while the bone tissue is subjected to a vacuum; and, enzymatic treatment to form chemical linkages at any collagen-collagent interface. The preferred method of forming chemical linkages is by chemical reaction.

Chemical crosslinking agents include those that contain bifunctional or multifunctional reactive groups, and which react with surface-exposed collagen of adjacent bone particles within the coherent mass. By reacting with multiple functional groups on the same or different collagen molecules, the chemical crosslinking agent forms an occlusive surface on the coherent mass which is impermeable to the ingrowth of soft tissue.

Chemical crosslinking involves exposing the bone particles presenting surface-exposed collagen to the chemical crosslinking agent, either by contacting a portion of the surface of the coherent mass of bone particles with a solution of the chemical crosslinking agent, or by exposing the surface to the vapors of the chemical crosslinking agent under conditions appropriate for the particular type of crosslinking reaction. Such conditions include an appropriate pH and temperature, and for times ranging from minutes to days, depending upon the level of crosslinking desired, and the activity of the chemical crosslinking agent. The resulting bone graft is then washed to remove all leachable traces of the chemical.

Suitable chemical crosslinking agents include mono- and dialdehydes, including glutaraldehyde and formaldehyde; polyepoxy compounds such as glycerol polyglycidyl ethers, polyethylene glycol diglycidyl ethers and other polyepoxy and diepoxy glycidyl ethers; tanning agents including polyvalent metallic oxides such as titanium dioxide, chromium dioxide, aluminum dioxide, zirconium salt, as well as organic tannins and other phenolic oxides derived from plants; chemicals for esterification or carboxyl groups followed by reaction with hydrazide to form activated acyl azide functionalities in the collagen; dicyclohexyl carbodiimide and its derivatives as well as other heterobifunctional crosslinking agents; hexamethylene diisocyante; sugars, including glucose, will also crosslink collagen.

Glutaraldehyde crosslinked biomaterials have a tendency to over-calcify in the body. In this situation, should it be deemed necessary, calcification-controlling agents can be used with aldehyde crosslinking agents. These calcification-controlling agents include dimethyl sulfoxide (DMSO), surfactants, diphosphonates, aminooleic acid, and metallic ions, for example ions of iron and aluminum. The concentrations of these calcification-controlling agents can be determined by routine experimentation by those skilled in the art.

When enzymatic treatment is employed, useful enzymes include those known in the art which are capable of catalyzing crosslinking reactions on proteins or peptides, preferably collagen molecules, e.g., transglutaminase as described in Jurgensen et al., *The Journal of Bone and Joint Surgery*, 79-A (2), 185–193 (1997), herein incorporated by reference.

Formation of chemical linkages can also be accomplished by the application of energy. One way to form chemical linkages by application of energy is to use methods known to form highly reactive oxygen ions generated from atmospheric gas, which in turn, promote oxygen crosslinks between surface-exposed collagen. Such methods include using energy in the form of ultraviolet light, microwave energy and the like. Another method utilizing the application of energy is a process known as dye-mediated photo-oxidation in which a chemical dye under the action of visible light is used to crosslink surface-exposed collagen.

Another method for the formation of chemical linkages is by dehydrothermal treatment which uses combined heat and the slow removal of water, preferably under vacuum, to achieve crosslinking of the bone-derived elements. The process involves chemically combining a hydroxy group from a functional group of one collagen molecule and a hydrogen ion from a functional group of another collagen molecule reacting to form water which is then removed resulting in the formation of a bond between the collagen molecules.

Upon being heated or crosslinked, the surface area which comes in contact with the heat or crosslinking agent becomes occluded, i.e., "skinned over", so that the average pore size of the treated surface area becomes substantially reduced to a pore size range small enough to prevent soft tissue ingrowth. This occlusion does not deleteriously effect the osteogenic potential of the bone particles underlying the occluded layer or the osteogenic potential of the bone particles located in the other untreated portions of the bone graft.

It has been observed that the duration of the heating and/or crosslinking operations can be adjusted to control the depth or thickness of the zone of impermeability to soft tissue ingrowth and thereby impart rigidity to the bone graft of this invention. In general, as the coherent mass of bone particles herein is subjected to the heating and/or crosslinking operations for increasing periods of time, the depth/thickness of the zone of impermeability increases. As the depth/thickness of the zone of impermeability increases, the zone further acquires rigidity. This rigidity allows the bone graft to support loads, e.g., compressive forces of up to about 200 MPa, over the area defined by the zone and to maintain the space underlying the zone. Thus, the bone graft of this invention can be employed in load-bearing situations.

In accordance with a further embodiment, one or more biocompatible substances can be applied to a portion of the surface area of the coherent mass to provide a microporous layer or film thereon which is impermeable to soft-tissue ingrowth and which is integral with the coherent mass. Suitable substances include the microporous membrane-forming liquid polymer systems disclosed in U.S. Pat. No. 5,368,859, the entire contents of which are incorporated by reference herein. U.S. Pat. No. 5,368,859 discloses a thermoplastic system comprising a solid biodegradable polymer or copolymer dissolved in a solvent which is nontoxic and water miscible, to form a liquid solution and a thermosetting system comprising reactive, liquid, oligomeric polymers which contain no solvents and which cure in place to form solids, usually with the addition of a curing catalyst. These liquid polymer systems can be applied to a portion of the surface area of the coherent mass and allowed to penetrate the surface area and solidify thereon to provide a microporous layer or film which is integral with the coherent mass and is impermeable to soft tissue ingrowth. The thickness of the layer or film can be increased to impart rigidity to the bone graft. The biocompatible substances can be applied by any suitable technique, e.g., by brushing the surface of the coherent mass with liquid biocompatible substance, by dipping the coherent mass in the liquid biocompatible substance, and the like. The biocompatible substance can be applied to the coherent mass in vivo, if desired.

The bone graft herein is intended to be applied at a bone repair site, e.g., one resulting from injury, defect brought about during the course of surgery, infection, malignancy or developmental malformation. The bone graft can be utilized in a wide variety of orthopaedic, periodontal, neurosurgical and oral and maxillofacial surgical procedures such as the repair of simple and compound fractures and non-unions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, tumor surgery, e.g., deficit filing, discectomy, laminectomy, excision of spinal cord tumors, anterior cervical and thoracic operations, repairs of spinal injuries, scoliosis, lordosis and kyphosis treatments, intermaxillary fixation of fractures, mentoplasty, temporomandibular joint replacement, alveolar ridge augmentation and reconstruction, inlay bone grafts, implant placement and revision, sinus lifts, etc. Specific bones which can be repaired or replaced with the bone-derived implant herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal and metatarsal bones.

At the bone repair site, the bone graft can be employed in the dry state or, where site conformation is desired, in the hydrated state. The dry or hydrated bone graft can be cut or sized if need be to conform to a site being repaired. The bone graft can be hydrated before, during or after implantation with a suitable biocompatible liquid, e.g., water, saline solution, etc., for a period of time ranging from about 1 to about 120 minutes depending on the density of the bone graft. After being hydrated, the bone graft becomes flexible yet retains its shape and much of its strength. The bone graft can be packaged in either the dried or wet state and stored for subsequent application. In some circumstances, it is preferable to package the bone graft in the wet state so that it is ready for immediate use at the surgical site. The bone graft can be implanted at the bone repair site, if desired, using any suitable affixation means, e.g., sutures, staples, bioadhesives, and the like.

The bone graft of this invention finds particular utility in the field of periodontal surgery such as extraction sockets and alveolar ridge augmentation. The bone graft is applied to a periodontal repair site, e.g., a tooth extraction socket, in such a manner that the zone of impermeability to soft tissue ingrowth lies above the bone line where soft tissue resides and the untreated portion of the bone graft is in contact with bone tissue. In this manner, soft tissue ingrowth above the bone line is prevented or abated, thus obviating the need for a GBR membrane and allowing for the slower growing bone tissue to populate the region lying below the bone line. This results in a more efficient, simpler surgical procedure, eliminates the cost of GBR membrane and its implantation drawbacks and reduces the likelihood of infection (as the native collagen of the bone particles does not have the same tendency as synthetic implants to act as a nidus for infection).

Referring to the drawings, FIGS. 1a–1f depict various embodiments of a bone graft according to the present invention configured and dimensioned in the shape of a plate 36, tunnel 58, ring 92, disk 74, tooth root 22 and pin 120, respectively. The shaded areas of the above-embodiments, namely, 40, 60, 90, 78, 24 and 122, in FIG. 1 depict the zone(s) of impermeability of each bone graft 36, 58, 92, 74, 22 and 120, respectively. It will be understood that the location of such impermeable zones is not limited to those areas depicted in the drawings. The unshaded areas of the above-embodiments, namely, 38, 62, 94, 76, 26 and 121 depict the non-impermeable zone(s) of each bone graft 36, 58, 92, 74, 22 and 120, respectively, which will preferably contact the host's bone tissue.

Figure 1A:
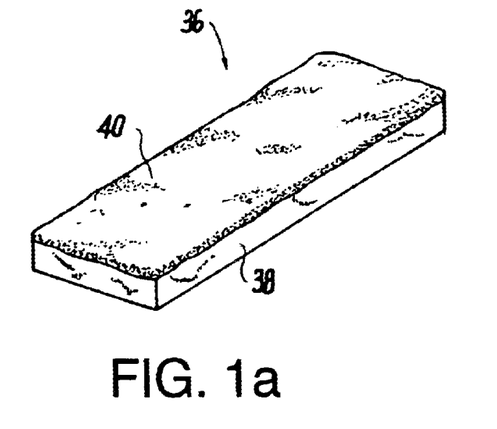
FIGS. 1a–1f show various configurations of a bone graft of the present invention.
Figure 1B:
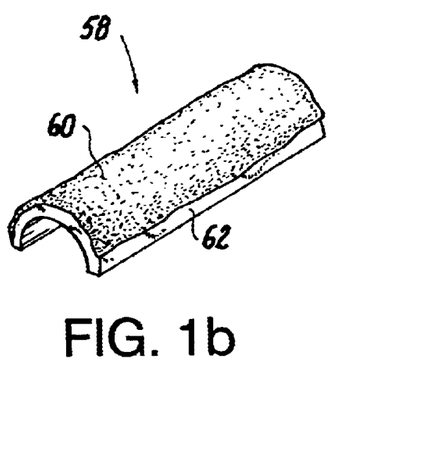
Figure 1C:
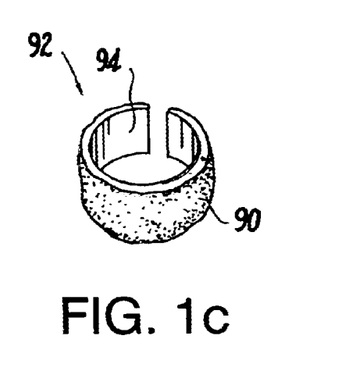
Figure 1D:
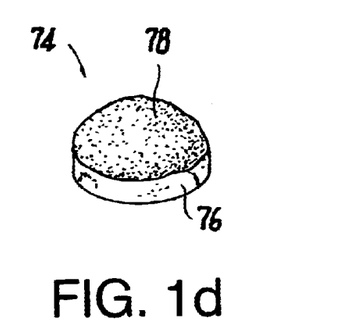
Figure 1E:
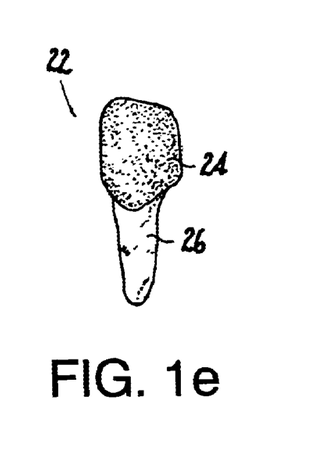
Figure 1F:
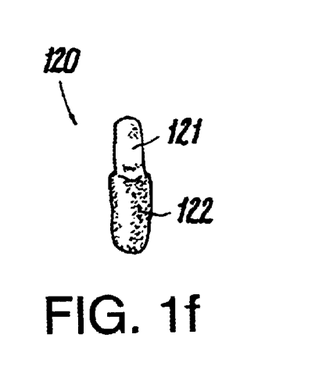
Figure 2A:
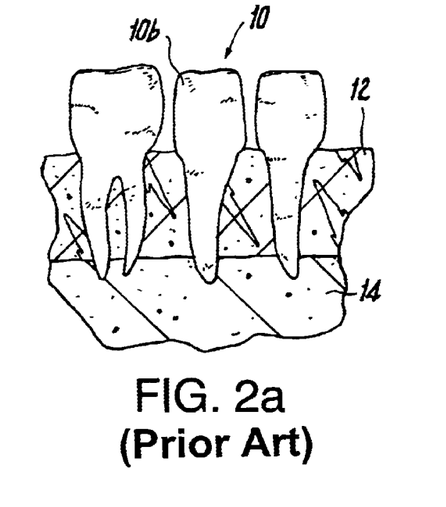
FIGS. 2a–2c schematically depict a prior art procedure for inducing bone growth in a periodontal extraction socket.
Figure 2B:
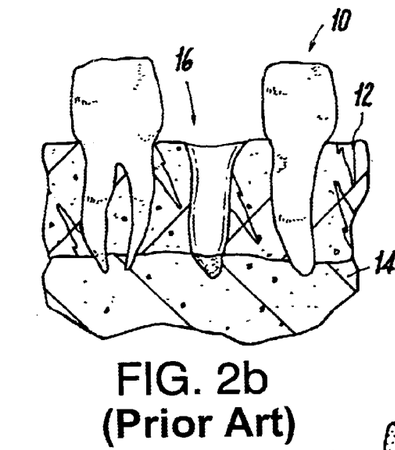
Figure 2C:
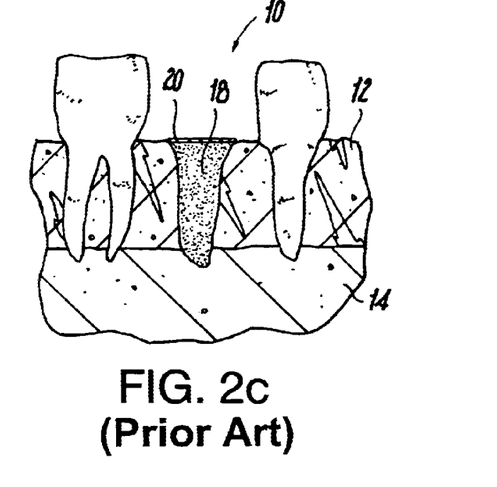

FIGS. 2a–2c depict a prior art process of inducing bone ingrowth in an extraction socket. Specifically, the middle tooth 10b of a plurality of teeth 10 is extracted from the host, thus exposing gingiva 12 and bone 14 and providing extraction socket 16. In accordance with currently employed periodontal techniques, extraction socket 16 is then filled with demineralized bone matrix 18 and covered with a barrier membrane 20 to prevent ingrowth of soft (gingival) tissue into the extraction socket 16. It is contemplated that barrier membrane 20 can also be placed on or along the inner walls of the extraction socket 16.

Figure 3A:
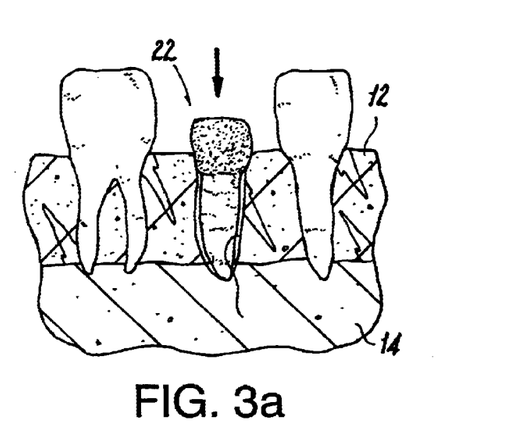
FIG. 3a schematically depicts a bone graft of the present invention being implanted into a periodontal extraction socket.
Figure 3B:
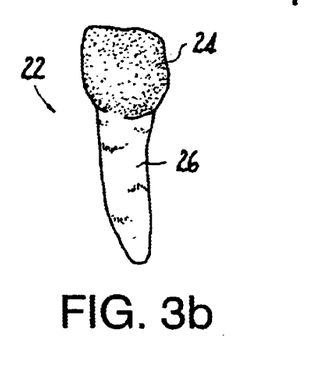

FIG. 3 depicts a preferred periodontal surgical procedure in accordance with the present invention. More particularly, after extraction of the tooth 10b, a bone graft 22 is implanted into the extraction socket 16. Preferably, in this particular embodiment, the bone graft 22 is configured and dimensioned in the shape of a tooth root as shown in FIG. 3b and includes a soft tissue impermeable zone 24 and a zone 26 which is in contact with bone. It is envisioned that the impermeable zone 26 of bone graft 22 comes into contact with bone 14 and induces new bone ingrowth which eventually remodels the bone graft 22 as the bone graft 22 is resorbed in vivo, thus providing a solid foundation for subsequent implant placement. Occlusive surface 24 prevents or abates the ingrowth of competitive, faster-growing soft (gingival) tissue into the extraction socket 16, thus allowing the slower-growing bone tissue to remodel bone graft 22.

Figure 4A:
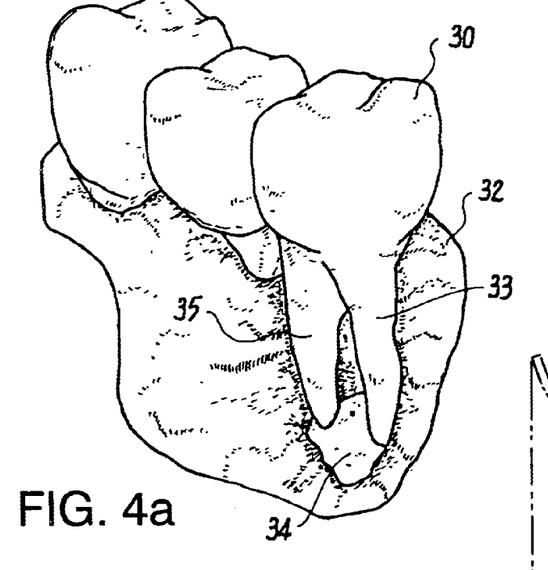
FIG. 4a is an isometric view of a furcation defect adjacent a tooth.
Figure 4B:
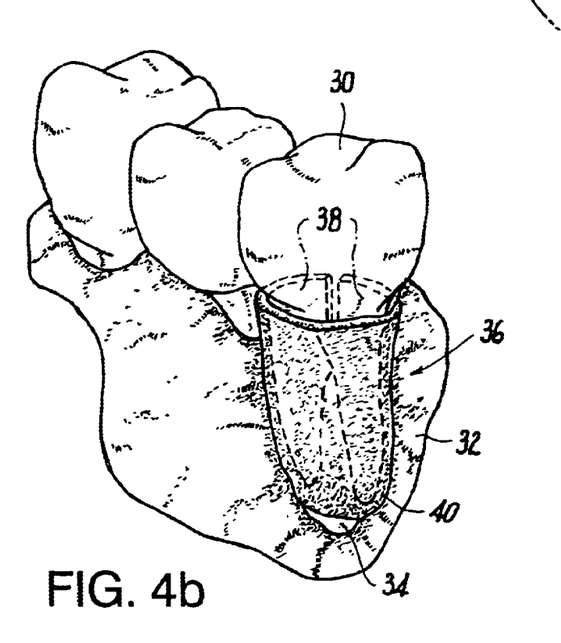
Figure 4C:
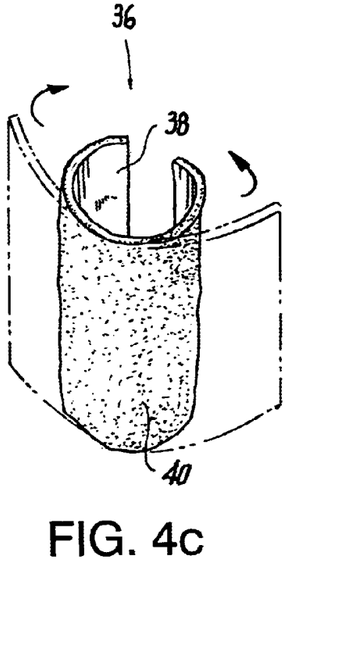

FIGS. 4a–4c depict another periodontal surgical procedure in accordance with the present invention which promotes bony ingrowth into a furcation defect 35. More particularly, a tooth 30 is depicted with a furcation defect 35, i.e., receded gingiva 32 and exposed root 33 surrounding tooth 30. In accordance with the present invention, a collar-like or ring-shaped bone graft 36 is implanted about the outer periphery of the tooth 30 and the gingiva 32. In particular, the outer soft-tissue impermeable zone 40 contacts the gingiva 32 and the inner non-impermeable zone 38 contacts tooth 30 and bone 34. When the bone graft 36 of the invention is rehydrated, the bone graft 36 becomes flexible and pliable and can be contoured into any desirable configuration. Thus, the prerehydrated bone graft 36 (phantomly illustrated in FIG. 4c) is rehydrated and contoured to form the collar-like or ring-shaped configuration.

Figure 5A:
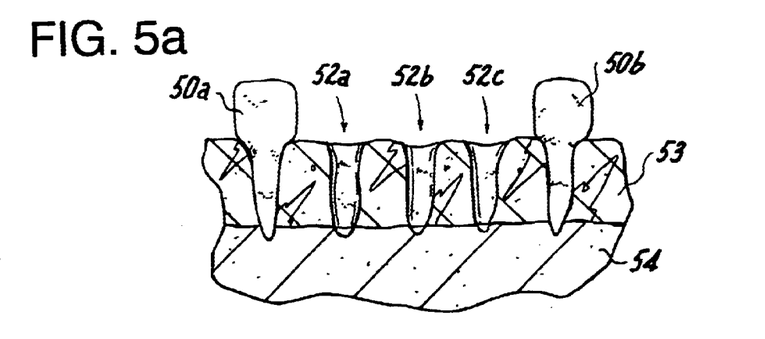
FIGS. 5a to 5d depict in sequential fashion a preferred periodontal surgical procedure for implanting a bone graft of the present invention atop a plurality of periodontal extraction sockets.
Figure 5B:
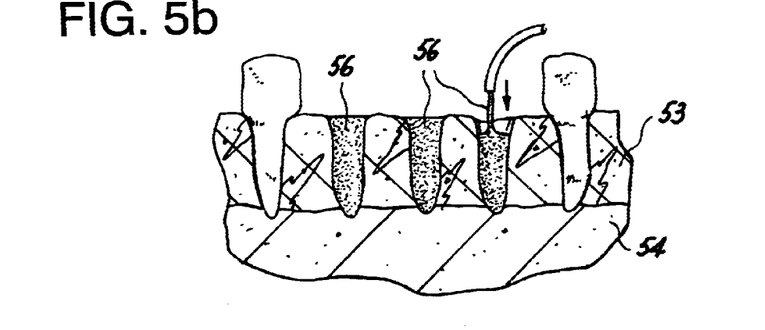
Figure 5C:
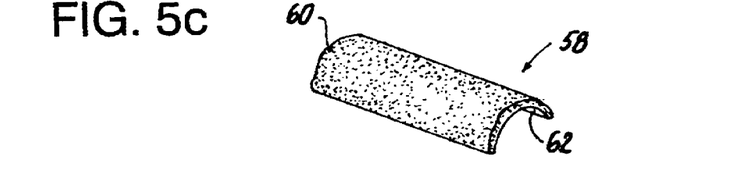
Figure 5D:
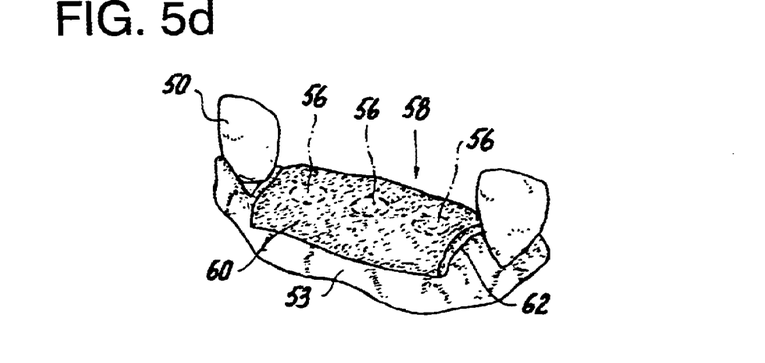

FIGS. 5a–5d depict another periodontal surgical procedure in accordance with the present invention wherein three teeth are removed to expose three extraction sockets 52a, 52b, and 52c. Preferably, bone 54 is exposed in each of the extraction sockets 52a, 52b and 52c. It is contemplated that the extraction sockets 52a, 52b, 52c are filled with demineralized bone matrix 56 in accordance with well known procedures, as shown best in FIG. 5b. Thereafter, a tunnel-shaped bone graft 58 is implanted over the DBM-filled extraction sockets 52a, 52b, 52c as depicted in FIG. 5d. As shown in FIG. 5c, bone graft 58 possess an outer soft-tissue impermeable zone 60 which is preferably rigid, i.e., capable of withstanding compressive forces of 50–200 MPa, and an inner non-impermeable zone which preferably contacts bone 54. The bone graft 58 protects the surrounding gingiva 53 from forces (such as mastication) which might displace DBM from the extraction sockets 52a, 52b, 52c.

Figure 6:
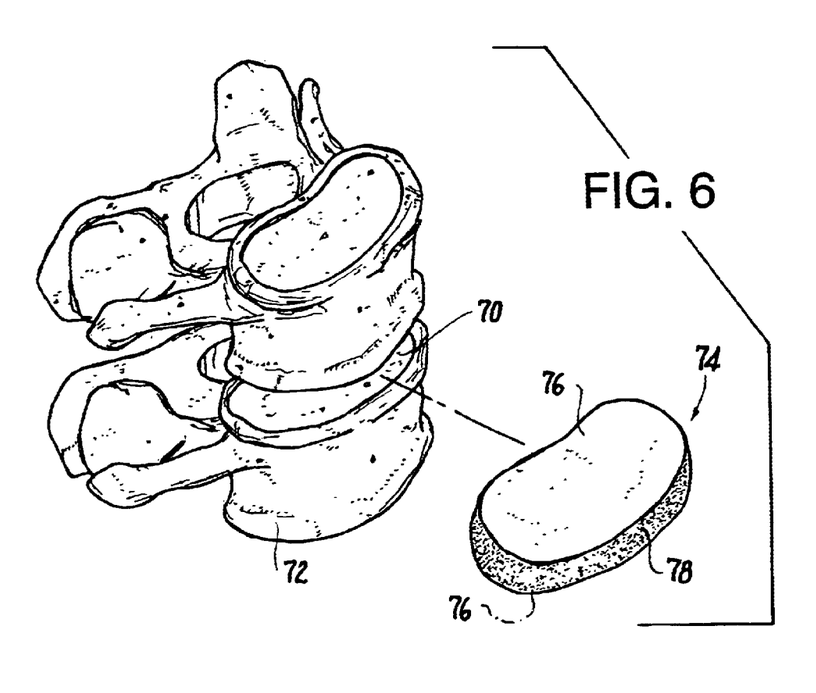
FIG. 6 is a fragmentarily-illustrated view of a vertebrae and a disc shaped bone graft positioned for installation at an intervertebral site.

As shown in FIG. 6, a disc-like bone graft 74 is configured and dimensioned to insert into the intervertebral fibrocartilage site 70 on the anterior side of vertebral column 72. Bone graft 74 possesses soft tissue impermeable zone 78 around the circumferential edge of graft 74 and non-impermeable surfaces 76 on the upper and lower sides of graft 74. It is envisioned that bone graft 74 blocks the migration of faster-growing epithelial cells at the intervertebral fibrocartilage site 70.

Figure 7:
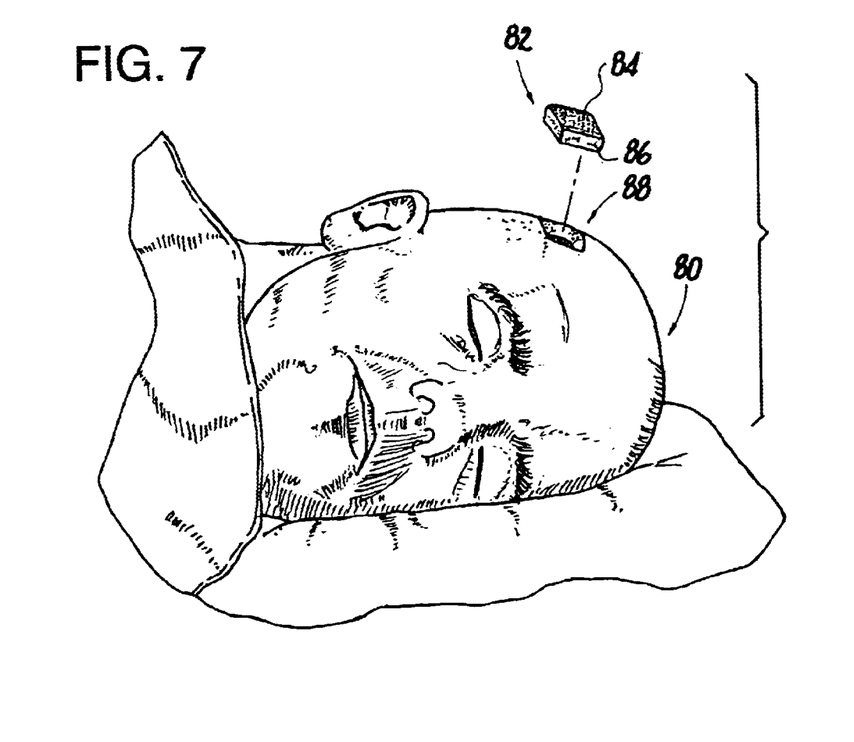
FIG. 7 is a schematic view of a human skull and a bone graft of the present invention positioned for implantation as a parietal bone replacement.

In FIG. 7, a bone graft 82 is sized and shaped to form part of the parietal bone 88 for skull 80. Bone graft 82 is provided with a soft tissue-occlusive surface 84 and a surface 86 which is non-occlusive with respect to soft-tissue. Surface 86 promotes fusion with parietal bone 88.

Figure 8:
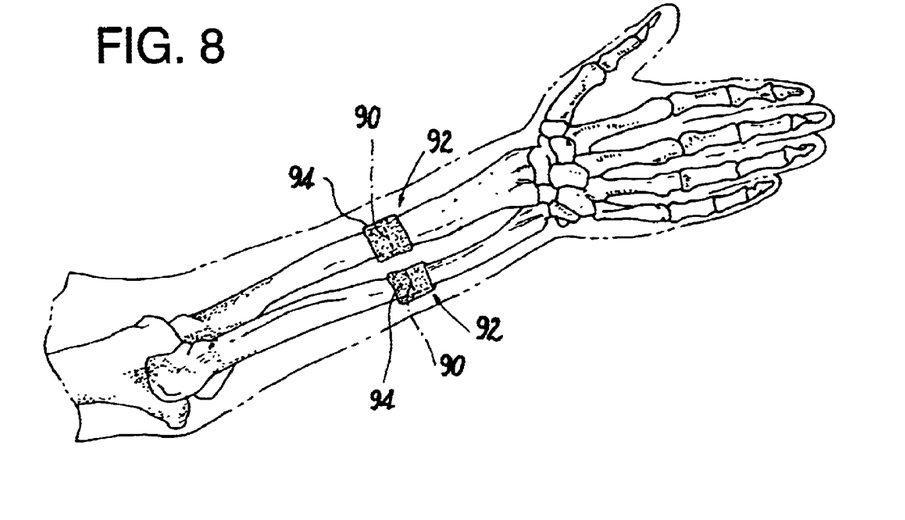
FIG. 8 is a schematic view of a human tibia and a fibula with a bone graft of the present invention implanted at a bone fracture site.

FIG. 8 depicts a collar-like bone graft 92 which includes an outer soft-tissue impermeable zone 90 and an inner surface 94 which promotes healing of fractures of the radius and ulna.

Figure 9:
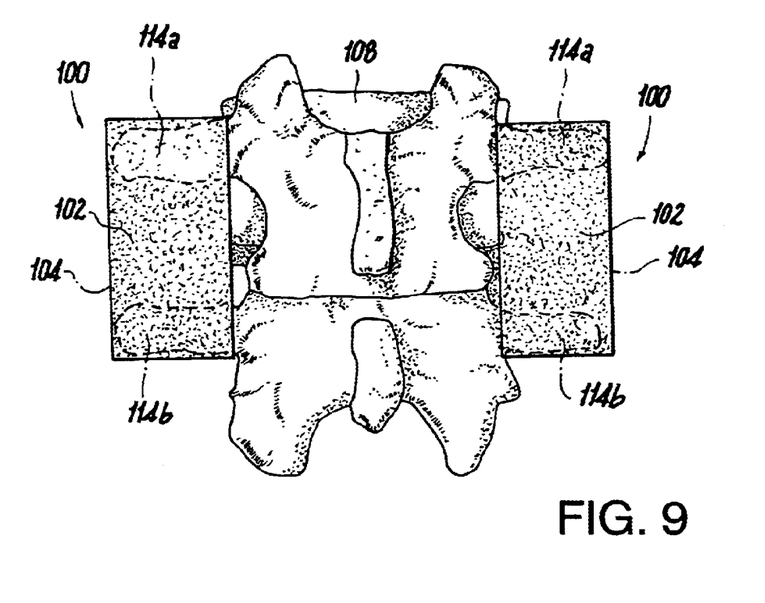
FIG. 9 is a posterior view of a vertebrae and a bone graft of the present invention positioned for implantation at a posterolateral intertransverse fusion site.

FIG. 9 shows sheet-like bone grafts 100 having an outer soft tissue impermeable zone 102 and an inner non-occlusive zone 104 which is preferably implanted as a spinal onlay graft bridging adjacent phantomly illustrated transverse processes 114a, 114b on vertebral column 108.

The present invention is intended to embrace all such devices which are constructed as the bone graft of the present invention and the attendant uses of such devices.

It will also be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The following examples are illustrative of the dental bone graft of this invention.

EXAMPLE 1

A bone graft of this invention possessing a conical shape which is configured and dimensioned to fit inside a tooth extraction socket was produced as follows.

Bovine bone fibers were fully demineralized in accordance with standard procedures and thereafter soaked in glycerol. After being soaked, the fibers were removed and collected on a sieve and excess glycerol was removed. The fibers were tightly packed into a 500-ul microcentrifuge tube possessing a 16 gauge opening at its tapered end, approximately the size and shape of a tooth extraction socket. Fibers were also tightly packed into a metal cap possessing a 16 gauge opening. The fiber-filled cap was then fitted over the fiber-filled tube. The metal cap portion is placed in a heating block with a small o-ring slipped over it to allow only the metal cap to be heated. The fibers in the metal cap are heated at 40–60° C. for 1 hour. The implant is then lyophilized for at least 24 hours. The resulting implant is removed from the mold.

EXAMPLE 2

To assess the permeability characteristics of the two zones of the bone graft of this invention, the following experiment was performed. A piece of bovine Grafton® Flex (available from Osteotech, Inc., Eatontown, N.J.) was heated on one surface against a smooth stainless steel surface at various temperatures and various times resulting in the heated surface becoming occluded as disclosed herein. This heating operation did not affect the other nonheated surface. A drop of water containing blue dye was then pipetetted onto the occluded surface area. The dye was unable to penetrate the occluded surface area suggesting a barrier characteristic. The piece of Grafton® Flex was then turned over and the blue dye was pipetetted on the unheated surface area. The dye readily became absorbed into the unheated surface area, demonstrating that it is a very permeable surface area.

What is claimed is:

1. An implantable, biocompatible osteogenic bone graft comprising a coherent mass of bone particles possessing at least one zone of impermeability to soft tissue ingrowth, said zone of impermeability being a porous region of the coherent mass of bone particles possessing pores having an average pore size which substantially prevents the ingrowth of bone tissue, wherein said zone is integral with the bone graft, such that the zone of impermeability and the bone graft are indivisibly connected so as to form a single unified whole.

2. The bone graft of claim 1 wherein the coherent mass of bone particles is configured and dimensioned in the shape of a tooth, tooth root, sheet, plate, disk, tunnel, ring, cone, pin, screw or tube.

3. The bone graft of claim 1 wherein the bone particles comprise from about 20 to about 100 weight percent of the coherent mass.

4. The bone graft of claim 1 wherein the bone particles comprise from about 30 to about 90 weight percent of the coherent mass.

5. The bone graft of claim 1 wherein the bone particles comprise from about 40 to about 85 weight percent of the coherent mass.

6. The bone graft of claim 1 wherein the bone particles are demineralized.

7. The bone graft of claim 6 wherein the demineralized bone particles are selected from the group consisting of superficially demineralized bone particles, partially demineralized bone particles, fully demineralized bone particles and mixtures thereof.

8. The bone graft of claim 1 wherein the bone particles are obtained from cortical, cancellous or cortico-cancellous types of bone, said types of bone being of autogenous, allogenic or xenogeneic origin.

9. The bone graft of claim 1 wherein the bone particles are obtained from porcine or bovine bone.

10. The bone graft of claim 1 wherein the bone particles are powdered.

11. The bone graft of claim 1 wherein at least about 60 weight percent of the bone particles possess a median length of from about 10 mm to about 100 mm, a median thickness of from about 0.02 mm to about 1 mm and a median width of from about 2 mm to about 5 mm.

12. The bone graft of claim 1 wherein the coherent mass further contains one or more substances selected from the group consisting of binders, fillers, plasticizers, biostatic agents, biocidal agents and surface active agents.

13. The bone graft of claim 1 wherein the coherent mass further contains at least one bioactive substance.

14. The bone graft of claim 1 where the coherent mass possesses a consistency which is shape sustaining but readily deformable.

15. The bone graft of claim 1 wherein the coherent mass is rigid and relatively strong when dry and flexible and pliable when wetted or hydrated.

16. A process for guided bone regeneration which comprises:
providing an implantable, biocompaatible osteogenic bone graft comprising a coherent mass of bone particles possessing at least one zone of impermeability to soft tissue ingrowth, said zone of impermeability being a porous region of the coherent mass of bone particles possessing pores having an average pore size which substantially prevents the ingrowth of bone tissue, wherein the zone is integral with the bone graft such that the zone of impermeability and the bone graft are indivisibly connected so as to form a single, unified whole; and
applying the bone graft to a bone repair site.

17. The process of claim 16 wherein the bone particles comprise from about 20 to about 100 weight percent of the coherent mass.

18. The process of claim 16 wherein the bone particles comprise from about 30 to about 90 weight percent of the coherent mass.

19. The process of claim 16 wherein the bone particles comprise from about 40 to about 85 weight percent of the coherent mass.

20. The process of claim 16 wherein the bone particles are demineralized.

21. The process of claim 20 wherein the demineralized bone particles are selected from the group consisting of superficially demineralized bone particles, partially demineralized bone particles, fully demineralized bone particles and mixtures thereof.

22. The process of claim 16 wherein the bone particles are obtained from cortical, cancellous or cortico-cancellous types of bone, said types of bone being of autogenous, allogenic or xenogeneic origin.

23. The process of claim 20 wherein the bone particles are obtained from porcine or bovine bone.

24. The process of claim 16 wherein the bone particles are powdered.

25. The process of claim 16 wherein at least about 60 weight percent of the bone particles possess a median length of from about 10 mm to about 100 mm, a median thickness of from about 0.02 mm to about 1 mm and a median width of from about 2 mm to about 5 mm.

26. The process of claim 16 wherein the coherent mass further contains one or more substances selected from the group consisting of binders, fillers, plasticizers, biostatic agents, biocidal agents and surface active agents.

27. The process of claim 16 wherein the coherent mass contains at least one bioactive substance.

28. The process of claim 16 where the coherent mass possesses a consistency which is shape sustaining but readily deformable.

29. The process of claim 16 wherein the coherent mass is rigid and relatively strong when dry and flexible and pliable when wetted or hydrated.

30. The process of claim 16 wherein the bone graft is configured and dimensioned in the shape of a tooth, tooth root, sheet, plate, disk, tunnel, ring, cone, pin, screw or tube.

31. The process of claim 16 wherein the coherent mass is configured and dimensioned to fit inside a tooth extraction socket.

32. The process of claim 16 wherein the bone repair site is a site associated with surgery, infection, malignancy or developmental malformation.

33. The process of claim 16 wherein the bone repair site is an orthopaedic, periodontal, neurosurgical, oral or maxillofacial bone repair site.

34. The process of claim 16 wherein the bone repair site is a periodontal bone repair site.

35. The process of claim 34 wherein the bone graft is in the shape of a tooth or tooth root.

* * * * *